United States Patent
Dunn et al.

(10) Patent No.: US 10,238,685 B2
(45) Date of Patent: Mar. 26, 2019

(54) COMPOSITIONS CONTAINING POLYMERIC SULFUR AND USES THEREOF

(71) Applicant: Johnson & Johnson Consumer Inc., Skillman, NJ (US)

(72) Inventors: Kelly Dunn, High Bridge, NJ (US); Ali Fassih, Franklin Park, NJ (US); Euen T. Ekman-Gunn, Hopewell, NJ (US); Wen-Hwa Li, Cranbury, NJ (US); Ramine Parsa, Lawrenceville, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 14/956,883

(22) Filed: Dec. 2, 2015

(65) Prior Publication Data

US 2017/0157170 A1   Jun. 8, 2017

(51) Int. Cl.
*A61K 33/04* (2006.01)
*A61Q 19/00* (2006.01)
(Continued)

(52) U.S. Cl.
CPC .............. *A61K 33/04* (2013.01); *A61K 8/23* (2013.01); *A61K 8/347* (2013.01); *A61K 8/368* (2013.01); *A61K 8/38* (2013.01); *A61K 8/447* (2013.01); *A61K 8/46* (2013.01); *A61K 9/0014* (2013.01); *A61K 31/05* (2013.01); *A61K 31/198* (2013.01); *A61K 31/235* (2013.01); *A61K 31/327* (2013.01); *A61K 31/60* (2013.01); *A61Q 19/00* (2013.01); *A61Q 19/007* (2013.01); *A61Q 19/08* (2013.01); *A61K 2800/30* (2013.01); *A61K 2800/596* (2013.01); *A61K 2800/74* (2013.01)

(58) Field of Classification Search
CPC .......... A61K 33/04; A61K 8/23; A61K 8/347; A61K 8/46; A61K 8/368; A61K 8/38; A61K 8/447; A61K 9/0014; A61K 31/05; A61K 31/198; A61K 31/235; A61K 31/327; A61K 31/60; A61K 2800/30; A61K 2800/596; A61K 2800/74; A61Q 19/00; A61Q 19/007; A61Q 19/08
See application file for complete search history.

(56) References Cited

U.S. PATENT DOCUMENTS 2,460,776 A    2/1949   Vincent
3,755,560 A    8/1973   Dickert
(Continued)

FOREIGN PATENT DOCUMENTS

DE    199 34 169 A1    1/2001
EP    0 281 812 A1    9/1988
(Continued)

OTHER PUBLICATIONS

22 Home Remedies for Acne & Pesky Pimples: retrieved form internet: http://everydayroots.com/acne-remedies. Retrieved on Oct. 29, 2016.*

(Continued)

*Primary Examiner* — Hong Yu (57) ABSTRACT

This invention relates to personal care compositions and methods of treating topical skin conditions using compositions containing polymeric sulfur $S_n$. The compositions of this invention may also preferably contain —SH-containing compounds such as thiols.

5 Claims, 4 Drawing Sheets (51) Int. Cl.

| | |
|---|---|
| *A61K 8/34* | (2006.01) |
| *A61K 9/00* | (2006.01) |
| *A61K 8/23* | (2006.01) |
| *A61K 31/05* | (2006.01) |
| *A61K 31/198* | (2006.01) |
| *A61Q 19/08* | (2006.01) |
| *A61K 8/46* | (2006.01) |
| *A61K 8/368* | (2006.01) |
| *A61K 8/38* | (2006.01) |
| *A61K 8/44* | (2006.01) |
| *A61K 31/235* | (2006.01) |
| *A61K 31/327* | (2006.01) |
| *A61K 31/60* | (2006.01) |

(56) References Cited

U.S. PATENT DOCUMENTS

| | | | | |
|---|---|---|---|---|
| 3,832,464 | A * | 8/1974 | Hennart | C07F 9/091 424/705 |
| 4,192,866 | A | 3/1980 | Anderson | |
| 4,254,105 | A | 3/1981 | Fukuda | |
| 4,421,769 | A | 12/1983 | Dixon | |
| 4,960,764 | A | 10/1990 | Figueroa, Jr. | |
| 5,654,362 | A | 8/1997 | Schulz, Jr. | |
| 5,891,424 | A | 4/1999 | Bretzler | |
| 5,919,437 | A | 7/1999 | Lee | |
| 5,976,514 | A | 11/1999 | Guskey | |
| 6,060,546 | A | 5/2000 | Powell | |
| 2008/0112909 | A1 * | 5/2008 | Faler | A61K 8/11 424/61 |
| 2017/0087180 | A1 * | 3/2017 | Giordano | A61K 33/04 |

FOREIGN PATENT DOCUMENTS

| WO | WO 2002/02059 A1 | 1/2002 |
|---|---|---|
| WO | WO 2010/000299 A1 * | 1/2010 |
| WO | WO 2011/044568 A1 | 4/2011 |
| WO | WO 2013/166585 A1 * | 11/2013 |

OTHER PUBLICATIONS

Allotropes of Sulfur: retrieved form internet: http://www.liquisearch.com/allotropes_of_sulfur. Retrieved on Oct. 29, 2016.*

Insoluble Sulphur (IS-90): retrieved from internet: http://www.wlchem.com/template/cp13_en.htm. Retrieved on Oct. 29, 2016.*

Insoluble sulfur CAS No. 9035-99-8: retrieved from internet: http://www.scienoc.com/insoluble_sulfur.html. Retrieved on Oct. 29, 2016.*

Chemistry of Sulfur: retrived from internet: http://chem.libretexts.org/Core/Inorganic_Chemistry/Descriptive_Chemistry/Elements_Organized_by_Block/2_p-Block_Elements/Group_16%3A_The_Oxygen_Family/Chemistry_of_Sulfur. Retrieved on Oct. 29, 2016.*

Sulfur Noodles (Allotropes of Sulfur): retireved from internet: https://chem.umn.edu/sulfur-noodles-allotropes-sulfur. Retrieved on Sep. 4, 2018.*

Bernhofer, et al., "The Influence of the Response of Skin Equivalent Systems to Topically Applied Consumer Products by Epithelial—Mesenchymal Interactions", Toxicology in Vitro, 219-229 (1999).

Choudhury et al., "Investigation of Antimicrobial Physiology of Orthorhombic and Monoclinic Nanoallotropes of Sulfur at the Interface of Transcriptome and Metabolome", Applied Microbiology and Biotechnology (2013) 97:5965-5978.

Cole, H.N., "Topical Therapy", Excerpta Medica, Belle Mead, NJ, vol. 14, No. 3, (Jan. 1, 1974) pp. 453-455, XP002044491.

Database TKDL [Online], Dec. 15, 2009, nn: "Sudha Parpati", XP002769053.

Database TKDL [Online], Jun. 15, 2012, nn: "Vajraoekhararasaa (Prathamaa)", XP002769054.

Database TKDL [Online], Dec. 15, 2009, nn: "Ma® ji °h dyamtailam (3)", XP002769055.

Database TKDL [Online], Dec. 15, 2009, nn: "Mamsi Taila", XP002769056.

European Search Report for Application No. EP 16 20 1966 completed Apr. 7, 2017.

* cited by examiner

COMPOSITIONS CONTAINING POLYMERIC SULFUR AND USES THEREOF

FIELD OF THE INVENTION

This invention relates to compositions containing polymeric sulfur and methods of use thereof. More particularly, this invention relates to mild compositions containing polymeric sulfur and amino acids containing a thiol group that are useful in the treatment and prevention of acne vulgaris, acne rosacea, other dermatological disorders; their manifestations in the skin; methods of using such compositions to treat acne vulgaris, rosacea, and various skin disorders; and provide antimicrobial efficacy.

BACKGROUND OF THE INVENTION

Acne is a common multi-factor pathology that attacks areas of the skin rich in sebaceous glands such as the face, shoulder area, arms and intertriginous areas. Acne is the most commonly occurring form of dermatosis. There are five pathogenic factors playing a determining role in the formation of acne: genetic predisposition; overproduction of sebum (seborrhea); androgens; follicular keratinization disorders (comedogenesis); and bacterial colonization and inflammatory factors. There are several forms of acne such as acne conglobata, keloid acne of the nape of the neck, acne medicamentosa, recurrent miliary acne, necrotic acne, neonatal acne, premenstrual acne, occupational acne, acne rosacea, senile acne, solar acne and common acne; the common factor of all being attack of the pilosebaceous follicles.

The various forms of acne described above can be treated with active agents. Such active agents include, without limitation, anti-seborrheic agents and anti-infectives, such as benzoyl peroxide and keratolytic agents including salicylic acid. Various compositions are used for cleansing the skin of acne patients. Preferably, such cleansers should not compromise the skin barrier or cause the skin to increase sebum production in reaction to drying or harsh ingredients.

Generally, anti-acne therapies may promote dry skin. However, such a tactic can produce skin barrier damage leading to an increased loss of water from the stratum corneum. An intact skin barrier is essential for the correct functioning of both the physical and chemical elements of the skin's protective mechanisms. Acne directly influences the skin barrier function via the inflammatory process and sebum overproduction. Excessive sebum production leads to imbalanced skin lipids and structural alterations in key barrier components such as fatty acids deficiency. Excessive sebum production also leads to depletion of cholesterol and ceramides, which, in turn, may lead to an increased TEWL (Trans Epidermal Water Loss). Skin barrier damage and increased TEWL can aggravate acne. Consequently, dermatologists recognize the value of moisturizers and cleansers as adjuncts to prescribed treatments.

Historically, sulfur has been used in several ways to promote skin health. The use of sulfur in a variety of dermatological products has been known for many years for treating acne. Dermatologists sometimes recommend topical sulfur ointments for treating dermatological disorders such as acne vulgaris, acne rosacea, mite infestations, seborrheic dermatitis, rosacea, eczema, and dandruff and other conditions. Sulfur has also been used topically to treat warts, pityriasis versicolor or skin discoloration, hair-follicle infections, and shingles. Sulfur appears to assist in shedding excessive skin and targeting bacteria on the skin. Patients usually apply sulfur products topically rather than consuming them orally. Topical forms of sulfur products are in the form of creams or ointments, cleansers, gels, lotions, and topical suspensions. However, as recognized in the art, there are several drawbacks associated with sulfur formulations.

First, sulfur may degrade into malodorous components, such as sulfanilamide. Chemical and physical stability of sulfur compositions has been difficult to achieve. Many sulfur compositions degrade, turn color, and become malodorous in a relatively short time, which is undesirable to consumers. It is desirable to have non-malodorous and aesthetically pleasing compositions.

Second, sulfur tends to irritate the skin and eyes. As levels of sulfur are increased in attempt to improve a sulfur product's efficacy, irritation also tends to increase, making sulfur less desirable for use on or near delicate skin and/or the eyes. For instance, users may experience side effects such as skin dryness, itching, swelling, and irritation while using sulfur to treat skin problems. Further, applying sulfur to broken, wounded, sunburned or otherwise irritated skin can worsen the irritation.

Sulfur exists at room temperatures primarily as rhombic crystals. Other forms of sulfur, such as monoclinic crystalline sulfur, or polymeric sulfur, are the normal primary forms which elemental sulfur assumes at certain higher temperature ranges. At room temperatures, these forms convert, or revert, to rhombic sulfur.

Certain attempts to decrease the irritancy and odor of sulfur include compounding sulfur with other sorptive materials such as gums, clays, silicates, etc. in order to promote stability of the sulfur. Sorptive materials, when applied topically to the skin, absorb irritants, such as sweat, sebum, oil, and dirt, from the skin. However, the stability provided by these sorptive materials is limited and often not conducive to cleanser compositions. Further, while some improvements have been made in mildness or odor reduction, additional improvements in mildness are desirable, particularly improvements in both mildness and the ability to maintain strong efficacy.

SUMMARY OF THE INVENTION

This invention provides compositions that overcome the disadvantage associated with sulfur-containing compositions and have relatively low irritation and sufficient antibacterial properties. In particular, the polymeric sulfur compositions of this invention have reduced irritation and enhanced antibacterial properties. Further, in certain embodiments of the compositions of this invention, the polymeric sulfur may further be combined with thiol-bearing compounds, for example, cysteine to produce compositions that exhibit even more significant antibacterial property.

Polymeric sulfur or polymerized sulfur consists of molecules formed from long chains of sulfur atoms, usually thousands of sulfur atoms per molecule. At room and processing temperatures, the chains of polymeric sulfur tend to revert to normal sulfur. Such reversion can be deterred by adding certain stabilizing agents in small quantities thus stabilizing the polymeric sulfur. The stabilized forms have dominated the market.

There are no known solvents for polymeric sulfur; therefore polymeric sulfur is also referenced as insoluble sulfur. Accordingly, one known disadvantage of including polymeric sulfur in a composition is that it is often hard to disperse.

Insoluble sulfur is an amorphous form of sulfur, which is made from the heat-polymerization of sulfur and also can be obtained by reacting hydrogen sulfide with sulfur dioxide. Insoluble sulfur is macromolecule polymer, and there are several thousand of sulfur atoms in its molecular chains. Because it does not dissolve in carbon disulfide, it is known as "insoluble sulfur" or "polymeric sulfur". Currently insoluble sulfur is mainly used in rubber industries.

Insoluble sulfur is an important rubber additive agent. It improves product quality, wearability and resistance to both fatigue and ageing. In addition to being universally recognized as the best vulcanizing agent, it is widely used in the manufacture of tire, rubber pipe, shoes, cable and wire insulating materials, latex, all kinds of automobile rubber parts, and is also a necessary component of belt tires. However, it is not known to be useful in topical skin compositions Sulfur exists in two forms represented by an equilibrium between a ring form of $S_8$ and its linear open chain form. Polymeric sulfur represents a much longer linear chain of sulfur atoms represented by $(-S-)_n$. Literature has shown that this can repeat for millions of repeat units. In any case, the fraction of a sulfur and polymeric sulfur sample may be determined by virtue of the solubility of both linear and cyclic $S_8$ in carbon disulfide, and the insolubility of polymeric sulfur in this solvent. A solubility-based method to characterize polymeric sulfur content is available by the Ministry of Chemical Industry of People's Republic of China (Method HG/T 2525-93).

Insoluble sulfur can be stabilized by the addition of various substances, notably the halogens. This stabilized insoluble sulfur tends to remain polymeric at room and processing temperatures but it reverts to normal sulfur at higher temperatures, which permits it to be useful in the vulcanization of rubber.

Insoluble sulfur is normally supplied by the sulfur manufacturers in discrete particles or powder. This powder is extremely fine, classically having a reported average particle size of 3 microns. These particles are considerably smaller than the particles of normal sulfur usually supplied. These smaller particles are desired because the dispersion of this form of insoluble sulfur is limited by the particle size supplied, unlike the dispersion of soluble sulfur. This very fine powder presents various processing difficulties. It tends to form dust clouds in the mixing room, which are both a health hazard and a safety hazard. Sulfur dust explosions are a known hazard in the rubber industry. A number of ways to reduce this dusting are mentioned in the literature. Also, the sulfur powder is difficult to disperse in rubber. The individual particles tend to agglomerate. Because of this, the powders are frequently mixed with a portion of a polymer or other matrix materials to form a master batch before being added to the final compound. These master batches usually contain fifty percent or more sulfur. This processing step adds to the cost. Since these discrete particles retain their identity during mixing, the best possible dispersion is limited by the size of the particles, unless their melting point is exceeded. However, when melted, the rate of reversion is very rapid and the reverted sulfur, of course, blooms, and the advantages of using insoluble sulfur are negated. In order to decrease the probability of explosion, oil is added to insoluble sulfur.

As noted above, polymeric sulfur is not conventionally used as a therapeutic agent to treat acne. In addition, in view of the need for special processing steps and conditions, polymeric sulfur is considered less desirable than elemental sulfur for inclusion in topical skin compositions.

In accordance with principles of the present invention, a topical composition comprising polymeric sulfur is provided for treating a variety of skin conditions.

We have found that compositions comprising, consisting essentially of and consisting of polymeric sulfur overcomes many of the objections to the use of elemental sulfur in topical skin compositions and, for example, results in a comparatively milder formulation. More particularly, in accordance with principles of this invention, a mild keratolytic composition comprising, consisting essentially of and consisting of polymeric sulfur is useful for treating skin inflammation. In accordance with this invention, topical compositions comprising, consisting essentially of and consisting of polymeric sulfur may applied to skin to treat a variety of skin conditions, dermatological diseases or disorders (including, but not limited to, acne, rosacea, or skin infections) or skin characteristics (including, but not limited to, pigmentation, hair growth regulation, skin texture, skin firmness, skin elasticity, skin vasculature, dark circles, cellulite), sebum regulation (e.g., increasing or decreasing sebum production), pore size and appearance, hydration of dermal and epidermal tissues, skin shine, dandruff, body odor, diaper rash, scarring, pain, itch, inflammation, and edema. Examples of skin, mucosal or nail infections include, but are not limited to, those due to susceptible pathogens such as acne, rosacea, impetigo, folliculitis, furunculosis, ecthyma, eczema, psoriasis, atopic dermatitis, herpes, epidermolysis bullosa, icthyosis, and infected traumatic lesions (e.g., ulcers, minor burns, cuts, abrasions, lacerations, wounds, biopsy sites, surgical incisions and insect bites), cold sores, canker sores, periodontal diseases, vaginal fungal, bacterial and/or viral infections, and nail fungal and/or bacterial infections.

In accordance with this invention, an antimicrobial composition comprising, consisting essentially of and consisting of polymeric sulfur may be applied to the skin of a human to inhibit bacteria *Propionibacterium acnes* (hereinafter, "*P. acnes*").

In accordance with this invention, a topical composition comprising, consisting essentially of and consisting of polymeric sulfur is formed for treating a variety of skin conditions. This invention further relates to methods of treating skin conditions using a topical composition comprising, consisting essentially of and consisting of polymeric sulfur.

The topical compositions of this invention containing polymeric sulfur further preferably comprise, consist essentially of and consist of a compound containing thiol group (that is, an —SH group) that is capable of producing hydrogen sulfide. Preferably, said thiol-containing compound is an amino acid or a thiol-containing peptide. More preferably, said thiol-containing compound is a cysteine compound.

These and other features and advantages of the present invention will be readily apparent from the following detailed description of the invention, the scope of the invention being set out in the appended claims.

DETAILED DESCRIPTION OF THE INVENTION

For people who suffer from inflammatory acne, the immune system over-reacts to the *P. acnes* bacteria and sends an abundance of white blood cells, which in turn can lead to symptoms of inflammatory acne vulgaris (e.g. Types 2, 3 and 4). Many of the individual components that make up the bacteria are easily recognized by the immune system as "enemy" molecules. This material includes components of the bacterial cell wall, like peptidoglycans, lipopolysaccharides and proteins. *P. acnes* is a bacterium that can colonize the skin and hair follicles. The *P. acnes* bacteria are the primary pathogenic agents responsible for acne vulgaris. *Propionibacterium acnes* (*P. acnes*) grows deep inside of pores, where it feeds on the sebum that is produced by the sebaceous glands which surround the base of the hair shaft. In most cases, *P. acnes* bacteria are partially responsible for acne symptoms. Several studies have indicated that specific strains of *P. acnes* bacteria are more commonly associated with acne vulgaris. However, other bacteria (e.g. *Staphylococcus* and *Corynebacterium*) can also reside in the follicle and on the surface of the skin.

Propionibacteria are members of the "gram-positive" classification of bacteria, which includes many other species of infectious bacteria. Gram-positive bacteria have thick cell walls that are rich in peptidoglycans and lipopolysaccharides, (sugar molecules attached to proteins and fatty acids). The DNA from *P. acnes* bacteria is recognized as foreign by the immune system, so *P. acnes* bacteria triggers a powerful immune response.

The root cause of acne is believed to be a faulty immune response in human skin. In particular, two main types of immune failure can lead to acne symptoms. The first type of immune failure is known as a hyper-sensitive response. In this situation, an individual's immune system reacts over-aggressively to the presence of bacteria present on the skin and produces large amounts of inflammatory cytokines. These inflammatory cytokines induce white blood cells to release destructive enzymes and free radicals into the site of inflammation. This causes unnecessary collateral damage to the surrounding tissue. This damage, in turn, often stimulates the production of more inflammatory cytokines and this can become a vicious cycle. In some cases, the damage can actually make it easier for the bacteria to proliferate.

The other main type of dysfunctional immune response occurs when an individual's white blood cells do not effectively destroy and process the bacteria that they encounter. Ideally, white blood cells engulf (phagocytize) all of the bacteria in which they come into contact. Once engulfed, the white blood cell isolates the bacteria into an intracellular compartment called a phagosome, and pumps toxic molecules and enzymes into this compartment. These molecules and enzymes kill the bacteria and digest it into small pieces. These pieces are then presented to the immune system, which uses them to design specific antibodies that specifically target the bacteria. In people who suffer from chronic, inflammatory infections (like acne vulgaris), they often have white blood cells that have a defect in this processing pathway. In these individuals, their white blood cells ingest bacteria normally, but their cells have an unusually difficult time killing the bacteria after eating them. If this occurs, the white blood cells will often continue to secrete significant amounts of inflammatory cytokines until they die in a process called apoptosis. As the white blood cells have not necessarily destroyed the invading bacteria, the bacteria may escape and keep proliferating.

Both of the above examples of immune system dysfunction are usually genetic in origin. The susceptibility to acne vulgaris is likely hereditary. Individuals whose parents experienced difficulty with acne vulgaris are at an increased risk of encountering acne symptoms.

The compositions of this invention relate to compositions and methods useful for treating a variety of skin conditions, including but not limited to acne vulgaris, comprising, consisting essentially of and consisting of polymeric sulfur.

We have unexpectedly discovered that according to the compositions and methods of this invention, polymeric sulfur compositions not only provide superior antimicrobial properties against *P. acnes* and other genus of bacteria, they surprisingly also exhibit low irritation and improved mildness to the skin. In one embodiment of the compositions of this invention, a composition comprising, consisting essentially of and consisting of polymeric sulfur exhibits an anti-inflammatory potential in human primary epidermal cells in vitro at less than 180 pg/ml (measured in accord with the procedure described herein below and in the Examples). Therefore, the polymeric sulfur-containing compositions have beneficially low irritation properties associated therewith. In contrast, the monomeric sulfur compositions exhibit an anti-inflammatory potential in human primary epidermal cells in vitro of greater than 220 pg/ml.

We have further discovered that compositions comprising, consisting essentially of and consisting of (a) polymeric sulfur and (b) a compound containing a thiol group (—SH), unexpectedly have even more profound antimicrobial properties.

Preferably, the compositions of this invention comprise, consist essentially of and consist of a mass ratio based on sulfur that is polymerized to an amino acid bearing a thiol group from about 1:1000 to about 100:1. More preferably, this ratio is from about 1:10 to about 10:1.

Preferably, the thiol-bearing compounds useful in the compositions and methods of this invention are amino acids containing a thiol group. More preferably, such compounds are cysteine compounds. Examples of cysteine compounds useful in the compositions and methods of this invention include, but are not limited to the following: acetylcysteine (INN), N-Acetyl-L-Cysteine, Carboxymethyl Cysteine, L-Cysteine, N-Acetyl-, 2-Hydroxybenzoate (Ester). L-Cysteine, N-Acetyl-L-Cysteine, N-acetyl-S-[(2E,6E)-3,7,11-trimethyl-2,6,10-dodecatrienyl]-L-Cysteine, N-(Aminoiminomethyl)-Cysteine, DL-L-Cysteine, ethyl ester, hydrochloride (1:1) cysteine (INN), L-Cysteine, Cysteine/Litchi Chinensis Fruit Extract, L-Cysteine Monohydrochloride, L-Cysteine, S-(Carboxymethyl)-DNA, Cysteine Salt, N-Guanyl-L-Cysteine, Oxoacetamide Carbocysteine, Procysteine and the like.

Preferably, the polymeric sulfur raw material useful in the compositions of this invention should be substantially free of non-cosmetic oils (such as kerosene, benzene and the like). Much commercially available polymeric sulfur is combined with oil for use in vulcanization processes for manufacturing tires. However, such a combination is undesirable for use in personal care compositions and products. Compositions used as personal care products may, however, contain oils that are acceptable for use in topical formulations. For example, oils useful in topical formulations include but are not limited to, soy oil, mineral oil USP, canola oil, jojoba oil and other plant-based oils such as coconut oil, palm oil $C_{12}$-$C_{15}$ alkyl benzoate and the like.

Preferably, the polymeric sulfur useful in the compositions and methods of this invention may be described as $S_n$ where n is at least 9. More preferably, n is greater than 100. The polymeric sulfur compounds useful in the compositions and methods of this invention are preferably linear, but may also be branched or cyclic in conformation.

Preferably, the compositions of this invention contain an amount of polymeric sulfur that is active in treating topical skin conditions. More preferably, polymeric sulfur is present in the compositions of this invention in an amount of from about 0.01 to about 20 percent by weight of the composition.

The compositions of this invention may also include resorcinol or a resorcinol compound such as resorcinol monoacetate. Preferably, if resorcinol is present in the compositions of this invention, it is present in an amount of about 2 weight percent. If resorcinol monoacetate is in the compositions of this invention, preferably, it is present in the amount of about 3 weight percent.

Preferably, the pH of the compositions of this invention should be 8 or lower so as to maintain the polymeric structure of the sulfur compounds useful herein. Preferably, the compositions of this invention contain from about 0.01 to about 20 percent by weight of sulfur compounds. The compositions of this invention may contain a combination of polymeric sulfur and soluble sulfur.

The polymeric compositions of this invention may further include one or more benefit agents or pharmaceutically-acceptable salts and/or esters thereof, the benefit agents generally capable of interacting with the skin to provide a benefit thereto. As used herein, the term "benefit agent" includes any active ingredient that is to be delivered into and/or onto the skin at a desired location, such as a cosmetic or pharmaceutical. The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed.

Examples of suitable benefit agents include those that provide benefits to the skin, such as, but not limited to, depigmentation agents; reflectants; amino acids and their derivatives; antimicrobial agents; allergy inhibitors; anti-acne agents; anti-aging agents; anti-wrinkling agents, antiseptics; analgesics; shine-control agents; antipruritics; local anesthetics; anti-hair loss agents; hair growth promoting agents; hair growth inhibitor agents, antihistamines; anti-infectives; anti-inflammatory agents; anticholinergics; vasoconstrictors; vasodilators; wound healing promoters; peptides, polypeptides and proteins; deodorants and antiperspirants; medicament agents; skin firming agents, vitamins; skin lightening agents; skin darkening agents; antifungals; depilating agents; counterirritants; hemorrhoidals; insecticides; enzymes for exfoliation or other functional benefits; enzyme inhibitors; poison ivy products; poison oak products; burn products; anti-diaper rash agents; prickly heat agents; vitamins; herbal extracts; vitamin A and its derivatives; flavenoids; sensates; anti-oxidants; hair lighteners; sunscreens; anti-edema agents, neo-collagen enhancers, film-forming polymers, chelating agents; antidandruff/seborrheic dermatitis/psoriasis agents; keratolytics; and mixtures thereof. The cleansing methods of the present invention may further comprise any of a variety of additional, optional steps associated conventionally with cleansing hair and skin including, for example, lathering, rinsing steps, and the like. The compositions of this invention may also include other active ingredients, such as salicylic acid or benzoyl peroxide in the amount effective to treat skin conditions in combination with the polymeric sulfur compositions of this invention, potentially containing salicylic acid from about 0.5 to about 2% by weight of the composition and/or benzoyl peroxide in an amount of from about 2.5 to about 10% by weight of the composition.

In accordance with this invention, the polymeric sulfur-containing compositions of this invention may be used to treat bacterial infections without the undesirable side effect of the monomeric (or elemental) sulfur discussed above. Polymeric sulfur has been shown to have antibacterial property against bacterial species, such as *P. acnes* and *Staphylococcus*. Further, its efficacy to kill *P. acnes* bacteria is enhanced with an increasing purity of the polymeric sulfur. The polymeric sulfur-containing compositions of this invention may also be used to treat yeast or fungal infections, including those caused by *Candida albicans*.

The topical compositions of this invention may contain a carrier, which should be a cosmetically and/or pharmaceutically acceptable carrier. The carrier should be suitable for topical application to the skin, should have good aesthetic properties and should be compatible with other components in the composition.

These product types may comprise several types of acceptable topical carriers including, but not limited to solutions, emulsions (e.g., microemulsions and nanoemulsions), gels, solids and liposomes. The following are non-limitative examples of such carriers. Other carriers can be formulated by those of ordinary skill in the art.

The topical compositions useful in accordance with this invention can be formulated as solutions. Solutions typically include an aqueous solvent (e.g., from about 50% to about 99.99% or from about 90% to about 99% of a cosmetically acceptable aqueous solvent).

Topical compositions useful in this invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients is known and may be used herein. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "INCI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72-73 (1972) and the INCI Handbook pp. 1693-1697.

The topical compositions useful in this invention formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, U.S. Pat. Nos. 3,755,560, 4,421,769, McCutcheon's Detergents and Emulsifiers, North American Edition, pp. 317-324 (1986), and the ICI Handbook, pp. 1673-1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. Nos. 4,254,105 and 4,960,764, are also useful in the subject invention. In general, such single or multiphase emulsions contain water, emollients, and emulsifiers as essential ingredients.

The topical compositions of this invention can also be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

The topical leave-on compositions of this invention may also be formulated as a suspension. In such a case, the compositions of this invention preferably contain a suspending agent. As used herein, the term "suspending agent" means any material known or otherwise effective in providing suspending, gelling, viscosifying, solidifying and/or thickening properties to the composition or which otherwise provide structure to the final product form. These suspending agents include gelling agents, and polymeric or nonpolymeric or inorganic thickening or viscosifying agents. Such materials will typically be solids under ambient conditions and include organic solids, silicone solids, crystalline or other gellants, inorganic particulates such as clays or silicas, or combinations thereof.

The concentration and type of suspending agent selected for use in the topical leave-on compositions of this invention will vary depending upon the desired product hardness, rheology, and/or other related product characteristics. For most suspending agents suitable for use herein, total concentrations range from about 0.1% to about 40%, more typically from about 0.1% to about 35%, by weight of the composition. Suspending agent concentrations will tend to be lower for liquid embodiments (e.g., pressurized or other liquid sprays, roll-ons, etc.) and higher for semi-solid (e.g., soft solids or creams) or solid stick or cleanser embodiments. Preferably, the suspending agents are present in the compositions of this invention in an amount from about 0.1% to about 40%; more preferably, the suspending agents are present in an amount from about 0.1% to about 30.

Non limiting examples of suitable suspending agents include hydrogenated castor oil (e.g., Castor wax MP80, Castor Wax, etc.), fatty alcohols (e.g., stearyl alcohol), solid paraffins, triglycerides and other similar solid suspending esters or other microcrystalline waxes, silicone and modified silicone waxes. Non limiting examples of optional suspending agents suitable for use herein are described in U.S. Pat. No. 5,976,514 (Guskey et al.), U.S. Pat. No. 5,891,424 (Bretzler et al.), which descriptions are incorporated herein by reference.

Other suitable suspending agents include silicone elastomers at concentrations ranging from about 0.1% to about 10%, by weight of the composition. Non-limiting examples of such silicone elastomer materials suitable for use as a suspending agent herein are described in U.S. Pat. No. 5,654,362 (Schulz, Jr. et al.); U.S. Pat. No. 6,060,546 (Powell et al.) and U.S. Pat. No. 5,919,437 (Lee et al.), which descriptions are incorporated herein by reference. These silicone elastomers materials can also be added for their skin feel or other cosmetic benefits alone, or for such benefits in combination with suspending agent benefits.

The topical compositions useful in the subject invention may contain, in addition to the aforementioned components, a wide variety of additional oil-soluble materials and/or water-soluble materials conventionally used in compositions for use on skin, hair, and nails at their art-established levels.

As acne infection is partly attributed to the presence of P. acnes bacteria, and as sulfur has shown efficacy against P. acnes bacteria, we propose that compositions containing polymeric sulfur may be used for the treatment of acne vulgaris-causing infection or inflammation. In general, it is understood by those of skill in the art that efficacy of an active ingredient against P. acnes is a good indication that such active ingredient will be effective in treating the condition of acne vulgaris. The methods of this invention comprise, consist essentially of and consist of applying the personal care compositions of this invention containing polymeric sulfur $S_n$ to the skin on a daily basis to treat topical skin conditions including, for example, acne vulgaris as well as other topical skin conditions including, but not limited to, acne, rosacea, or skin infections or skin characteristics (including, but not limited to, pigmentation, hair growth regulation, skin texture, skin firmness, skin elasticity, skin vasculature, dark circles, cellulite, sebum regulation (e.g., increasing or decreasing sebum production), pore size and appearance, hydration of dermal and epidermal tissues, skin shine, dandruff, body odor, diaper rash, scarring, pain, itch, inflammation, and edema. Examples of skin, mucosal or nail infections include, but are not limited to, those due to susceptible pathogens such as acne, rosacea, impetigo, folliculitis, furunculosis, ecthyma, eczema, psoriasis, atopic dermatitis, herpes, epidermolysis bullosa, icthyosis, and infected traumatic lesions (e.g., ulcers, minor burns, cuts, abrasions, lacerations, wounds, biopsy sites, surgical incisions and insect bites), cold sores, canker sores, periodontal diseases, vaginal fungal, bacterial and/or viral infections, and nail fungal and/or bacterial infections.

As used herein, compositions that are "mild to the skin" refer to compositions that have low skin irritancy properties as indicated by: a) a relatively high Trans-epithelial Permeability (hereinafter, "TEP") value as determined in accordance with the TEP Test set forth herein; and/or b) a passing score in the screening tests: cell viability; cell lysis; and cytokine release (IL-1∝ and IL-1ra) performed in accordance with the Skin Assay Test as set forth herein.

As used herein, a composition that is "mild to the eyes" refers to compositions that possess a relatively high TEP value as determined in accordance with the TEP Test as set forth herein.

As used herein, a composition that is "substantially free of ocular sting" or "substantial lack of ocular sting" refers to compositions that possess relatively low sting values as determined in accordance with the Ocular Sting Test as set forth herein.

Skin Assay Test

Mildness is determined using a skin equivalent model as described by Bernhofer, et al., Toxicology in Vitro, 219-229 (1999), which is incorporated herein by reference. This model utilizes sequential screens for determining cell viability, cell lysis and cytokine release in order to evaluate the mildness of a surfactant system to the skin. Cell viability is determined using an AlamarBlue® assay, which is an indicator of metabolic activity. Cell lysis is detected by measuring lactate dehydrogenase (LDH) activity released from the cytosol of damaged cells. Cytokine release (both IL-1α and IL-1ra) is measured for those sample sets which do not exhibit loss of cell viability or cell lysis.

In general, a EpiDerm® Epi-100 human epidermal model is obtained from MatTek Corporation (Ashland, Mass. USA) and maintained according to the manufacturers' instructions. Normal human-derived epidermal keratinocytes (NREK) are then cultured to form a multilayered differentiated model of the epidermis. After a set of NREKs is exposed in triplicate to 100 µl of a topically applied surfactant sample, it is incubated for about 1 hour. After incubation, the set is washed five times, 400 µl per wash, with phosphate buffered saline (PBS), placed onto a fresh assay media, and returned to the incubator for about 24 hours.

Cell viability of the NREKs is determined 24 and 48 hours post treatment with the AlamarBlue® assay (Alamar Biosciences. Sacramento. Calif. USA) in accordance with manufacturers' protocols and a Cytofluor II Fluorescent Plate Reader (PerSeptive Biosystems. Framingham. Mass. USA). Cell lysis is determined colorimetrically using an LDH cytotoxicity detection kit (Boehringer-Mannheim). Cytokine content is measured using human calorimetric ELISA kits for IL-1α (ENDOGEN. Cambridge, Mass. USA), interleukin-1 receptor antagonist (IL-1ra, R&D Systems. Minneapolis. Minn. USA), granulocyte macrophage colony stimulating factor (GM-CSF). interleukin-6 (IL-6), interleukin-8 (IL-8). interleukin-IO (IL-b) and TNFα (PerSeptive Diagnostics. Cambridge, Mass. USA).

Ocular Sting Test

Using a double-blinded, randomized, two (2) cell study test design, one (1) drop of a sample (e.g. a 10% dilution of a cleansing composition in water) at a temperature of about 38° C. is instilled into a subject's eye. A new sterile disposable eyedropper is used for each sample and disposed of after being used on only one individual's eye. All instillations are performed either by an investigator or by a trained technician.

Within 30 seconds, or as closely as possible following instillation, the subject is asked to grade the perceived stinging sensation to the eye utilizing the following criteria:

Sting

0=Within normal limits

1=Mild, very slight

2=Moderate

3=Severe

After 15 minutes and 60 minutes post-instillation, the subject is again asked to grade the perceived stinging sensation to the eye.

Trans-Epithelial Permeability Test ("TEP Test"):

Irritation to the eyes expected for a given formulation is measured in accordance with the Invittox Protocol Number 86, the "Trans-epithelial Permeability (TEP) Assay" as set forth in Invittox Protocol Number 86 (May 1994). In general, the ocular irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the EC50 (the concentration of test material that causes 50% of maximum dye leakage, i.e., 50% damage to the permeability barrier). Higher scores are indicative of milder formulas.

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

The following examples demonstrate certain embodiments of the invention, however, they are not to be interpreted as limiting the scope of the invention, rather as contributing to a complete description of the invention.

EXAMPLES

Example 1

Antimicrobial Efficacy Test—Microcentrifuge Tube Method

For efficacy studies against *Propionibacterium acnes*, *Staphylococcus aureus*, and *Escherichia coli* 1% test sample suspensions [Sulfur (S) Sigma or Polymeric Sulfur ($S_n$) IS90 from Wuxi Wanli Chemical, China] were prepared as w/v in Butterfield's Phosphate Buffer. Serial dilutions of 1:10 were performed v/v for lower concentrations. Aliquots were then pipetted into microcentrifuge tube for exposure to test organism. Concentrations of 10% and 5% for testing against *Aspergillus brasiliensis* were weighed and diluted directly in microcentrifuge tubes.

Each test organism was standardized to concentration of 10E6 cfu/ml. Test sample was inoculated as 1:10 (0.1 ml inoculum to 0.9 ml sample) for final concentration of 10E5 cfu/ml sample. Buffer control sample was included and used to calculate log reduction for each test sample.

After inoculation, study tubes were placed at 37° C. (±2° C.), shaking at 1000 rpm for set exposure time (30 minutes, 1 hour or 3 hours). At completion of exposure time, each tube was centrifuged for 10 seconds to settle test material out of suspension. Aliquot of fluid was removed, serial diluted and plated for recovery of viable organisms.

Each organism was plated on appropriate media and incubated at proper temperature and length of time before counting recoveries.

*Propionibacterium acnes* ATCC 6919 anaerobic, gram-positive bacteria 30 minute exposure

| Sample | cfu/ml | Log | log reduction |
|---|---|---|---|
| Inoculum | 2.6E+05 | 5.4 | n/a |
| 1% $S_n$ | 1.4E+03 | 3.2 | 2.2 |
| 0.1% $S_n$ | 2.5E+04 | 4.4 | 1.0 |
| 0.01% $S_n$ | 9.6E+04 | 5.0 | 0.4 |
| 0.001% $S_n$ | 1.7E+05 | 5.2 | 0.2 |
| 1% S | 1.6E+05 | 5.2 | 0.2 |
| 0.1% S | 1.8E+05 | 5.3 | 0.1 |
| 0.01% S | 1.9E+05 | 5.3 | 0.1 |
| 0.001% S | 2.0E+05 | 5.3 | 0.1 |
| Buffer Ctrl | 1.9E+05 | 5.3 | 0.1 |

Conclusion: Data for *P. acnes* shows Polymeric Sulfur to have superior antimicrobial efficacy at 1% and 0.1% than the corresponding level of Sulfur. Neither form was efficacious in this study at 0.01% or 0.001%.

*Staphylococcus aureus* ATCC 6538 aerobic, gram-positive bacteria 60 minute exposure

| Sample | cfu/ml | Log | log reduction |
|---|---|---|---|
| Inoculum | 2.5E+05 | 5.4 | n/a |
| 1% $S_n$ | 4.3E+04 | 4.6 | 0.8 |
| 0.1% $S_n$ | 2.7E+03 | 3.4 | 2.0 |
| 0.01% $S_n$ | 7.3E+02 | 2.9 | 2.5 |
| 0.001% $S_n$ | 6.3E+02 | 2.8 | 2.6 |
| 1% S | 2.1E+05 | 5.3 | 0.1 |
| 0.1% S | 3.0E+03 | 3.5 | 1.9 |
| 0.01% S | 1.0E+04 | 4.0 | 1.4 |
| 0.001% S | 9.1E+03 | 4.0 | 1.4 |
| Buffer Ctrl | 9.4E+04 | 5.0 | 0.4 |

Conclusion: Against *S. aureus*, Polymeric Sulfur was superior to Sulfur at 1%, 0.01% and 0.001% test concentrations. At 0.1% the forms were equivalent.

*Escherichia coli* ATCC 8739 aerobic, gram-negative bacteria 30 minute exposure

| Sample | cfu/ml | Log | log reduction |
|---|---|---|---|
| Inoculum | 1.7E+06 | 6.2 | n/a |
| 1% $S_n$ | 4.1E+05 | 5.6 | 0.6 |
| 0.1% $S_n$ | 8.9E+05 | 5.9 | 0.3 |
| 0.01% $S_n$ | 1.0E+06 | 6.0 | 0.2 |
| 0.001% $S_n$ | 1.3E+06 | 6.1 | 0.1 |
| 1% S | 1.5E+06 | 6.2 | 0.0 |
| 0.1% S | 1.4E+06 | 6.1 | 0.1 |
| 0.01% S | 1.3E+06 | 6.1 | 0.1 |
| 0.001% S | 1.3E+06 | 6.1 | 0.1 |
| Buffer Ctrl | 1.3E+06 | 6.1 | 0.1 |

Conclusion: Against *E. coli*, Polymeric Sulfur was superior to Sulfur at 1% test concentration. Neither form was efficacious at 0.1%, 0.01% or 0.001% in this test.

*Aspergillus brasiliensis* ATCC 16404 spore forming fungi 3 hour exposure

| Sample | cfu/ml | Log | log reduction |
|---|---|---|---|
| Inoculum | 2.7E+05 | 5.4 | n/a |
| 10% $S_n$ | 2.9E+03 | 3.5 | 1.9 |
| 5% $S_n$ | 2.3E+04 | 4.4 | 1.0 |
| 1% $S_n$ | 1.7E+05 | 5.2 | 0.2 |
| 0.1% $S_n$ | 9.5E+04 | 5.0 | 0.4 |
| 10% S | 2.8E+05 | 5.4 | 0.0 |
| 5% S | 2.9E+05 | 5.5 | −0.1 |
| 1% S | 2.0E+05 | 5.3 | 0.1 |
| 0.1% S | 3.2E+05 | 5.5 | −0.1 |

Conclusion: Against *A. brasiliensis*, Polymeric Sulfur was superior to Sulfur at 10% and 5% test concentrations. Neither was efficacious at 1% or 0.01% in this method.

Example 2

Antimicrobial Efficacy Test—Tissue Culture Insert Method

For this method, a tissue culture insert maintains a physical separation of the sulfur particles from the outer fluid containing microorganism. The bottom of the tissue culture insert is permeable (4 μm pores) allowing fluids, dissolved solids and microorganisms to transfer back and forth.

Each test organism was standardized to concentration of 10E8 cfu/ml and diluted to 10E5 cfu/ml for inoculum. A buffer control sample was included and used to calculate log reduction for each test sample.

Each test sample was prepared just before addition of test organism. A stock solution of L-cysteine 200 mM was prepared by weighing 0.055 g into scintillation vial with 2.28 ml Phosphate Butterfield's Buffer.

For 1% suspension of sulfur or polymeric sulfur, 0.008 g was weighed directly into tissue culture insert; 0.1 ml of L-cysteine stock solution was added along with 0.092 ml Phosphate Butterfield's Buffer.

For 0.1% suspension of sulfur or polymeric sulfur, 0.001 g was weighed directly into tissue culture insert; 0.1 ml of L-cysteine stock solution was added along with 0.099 ml Phosphate Butterfield's Buffer.

The outer well of each tissue culture insert was inoculated with 0.6 ml of 10E5 cfu/ml inoculum. Tissue culture wells were sealed and held for 3 hours at 37° C. (±2° C.).

After exposure, the tissue culture insert containing sulfur was removed; external fluid was collected, serially diluted, and plated for recovery of viable organisms. The organism was plated on appropriate media and incubated at proper temperature and length of time before counting recoveries.

| Propionibacterium acnes ATCC 6919 anaerobic, gram-positive bacteria 3 hour exposure | | |
|---|---|---|
| Sample | Log | log reduction |
| Inoculum | 5.4 | n/a |
| 1% $S_n$ + 25 mM L-cysteine | 1.6 | 3.8 |
| 0.1% $S_n$ + 25 mM L-cysteine | 4.3 | 1.1 |
| 1% S + 25 mM L-cysteine | 4.3 | 1.1 |
| 0.1% S + 25 mM L-cysteine | 5.0 | 0.4 |
| Buffer Ctrl | 5.3 | 0.1 |

Conclusion: Polymeric Sulfur at 1% and 0.1% concentrations in presence of L-cysteine were significantly more efficacious at killing P. acnes than equal concentrations of Sulfur with L-cysteine in this study.

Example 8: Anti-Inflammation

| Polymeric sulfur | Regular sulfur | Lonza KGM-Gold Bullet Kit without hydrocortisone | IL-22 |
|---|---|---|---|
| 0.01% | 0% | 99.99% | 20 ng/ml |
| 0.1% | 0% | 99.9% | 20 ng/ml |
| 0.3% | 0% | 99.7% | 20 ng/ml |
| 1% | 0% | 99% | 20 ng/ml |
| 3% | 0% | 97% | 20 ng/ml |
| 0% | 0.01% | 99.99% | 20 ng/ml |
| 0% | 0.1% | 99.9% | 20 ng/ml |
| 0% | 0.3% | 99.7% | 20 ng/ml |
| 0% | 1% | 99% | 20 ng/ml |
| 0% | 3% | 97% | 20 ng/ml |

The anti-inflammatory potential of polymeric sulfur ($S_n$) and of regular sulfur (S) were evaluated in-vitro in human primary epidermal cell cultures. Normal human epidermal keratinocytes were purchased from Promocell (Heidelberg, Germany). The cells were plated in 24-well tissue culture treated plates at a density of 30,000 cells/well in Lonza KGM-Gold Bullet Kit without hydrocortisone (Lonza, Walkersville, Md.). After 48 hours, cells were treated with the actives described below: Polymeric form of sulfur (IS-90, Wuxi Wanli Chemical, China) and the regular form of sulfur (Sigma-Aldrich, St Louis, Mo., USA) at indicated concentrations, either in the presence or absence of the pro-inflammatory cytokine IL-22 (R&D Systems, Minneapolis, Minn.) 20 ng/ml. Following the treatment period of 24 hrs, the cell culture media supernatants were collected and analyzed for IL-8 cytokine release using MILLIPLEX®MAP kit (Millipore Corp., Billerica, Mass.).

Figure 1:
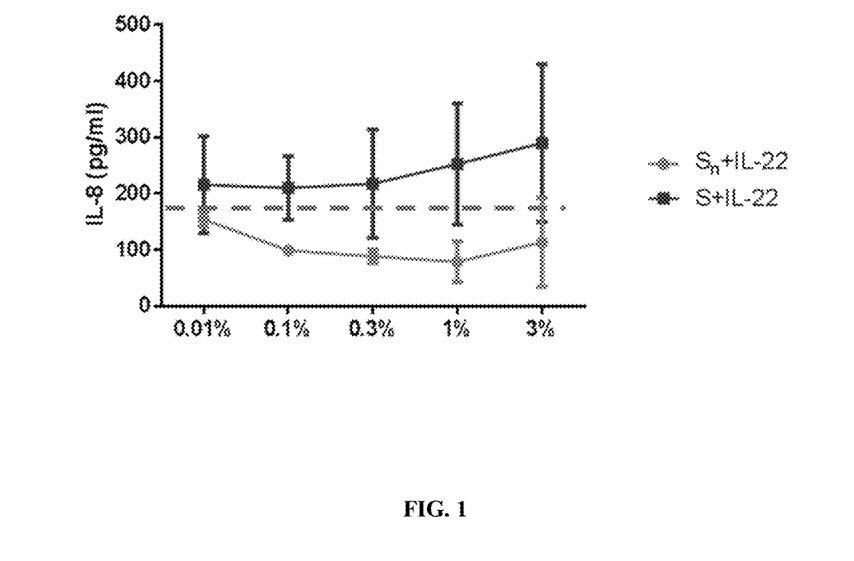
FIG. 1 is a graph depicting the results of an assay measuring the stimulation of the pro-inflammatory cytokine IL-8 above the values of the untreated control cells (dotted line) in presence of 20 ng/ml IL-22 in the presence of the regular form of sulfur (S), when used at doses ranging from 0.01% up to 3%, but not in the presence of polymeric sulfur ($S_n$).

In FIG. 1, the regular form of sulfur (S), when used at doses ranging from 0.01% up to 3%, did induce significantly the stimulation of the pro-inflammatory cytokine IL-8 above the values of the untreated control cells in presence of IL-22 (depicted by the dotted blue line). In contrast, the polymeric form of sulfur ($S_n$), inhibited significantly the IL-22-induced production of the pro-inflammatory cytokine IL-8 at the same doses tested from 0.01% up to 3%, below the values obtained for regular sulfur and those obtained for the untreated control cells in presence of IL-22. Conclusion:

Polymeric sulfur at 0.01-3% was more efficacious in inhibiting IL-22-induced IL-8 cytokine release than those of regular sulfur in human keratinocytes in vitro.

Example 9: Mildness

Example 9A: Mildness: Comparison of Pro-Inflammatory Cytokine Release IL-1α by Polymeric Sulfur ($S_n$) Vs Regular Sulfur (S) in Human Skin Equivalents

| Polymeric sulfur | Regular sulfur | 30% propylene glycol/70% ethanol | SDS (Sodium dodecyl sulfate) | Water |
|---|---|---|---|---|
| 0.1% | 0% | 99.9% | 0% | 0% |
| 1% | 0% | 99% | 0% | 0% |
| 10% | 0% | 90% | 0% | 0% |
| 0% | 0.1% | 99.99% | 0% | 0% |
| 0% | 1% | 99.9% | 0% | 0% |
| 0% | 10% | 99.7% | 0% | 0% |
| 0% | 0% | 0% | 10% | 90% |

The potential to induce the pro-inflammatory cytokine release IL1-a by either the polymeric sulfur ($S_n$) and of regular sulfur (S) were evaluated in human skin equivalents. Human skin equivalents (EPI 200 HCF-PRF), multilayer and differentiated epidermis consisting of normal human epidermal keratinocytes, were purchased from MatTek (Ashland, Mass.). Upon receipt, skin equivalents were incubated for 24 hours at 37° C. in maintenance medium without hydrocortisone. Equivalents were topically treated (0.1%, 1% and 10%) with either polymeric sulfur (IS-90, Wuxi Wanli Chemical, China) or regular sulfur (S, Sigma-Aldrich, St Louis, Mo., USA) in 70% ethanol/30% propylene glycol vehicle, and compared to either vehicle alone used as negative control, or to the 10 mM SDS used as positive control. Equivalents were incubated for 48 hours at 37° C. with maintenance medium then supernatants were analyzed for IL-1α pro-inflammatory cytokine release using MILLIPLEX®MAP kit (Millipore Corp., Billerica, Mass.).

Figure 2:
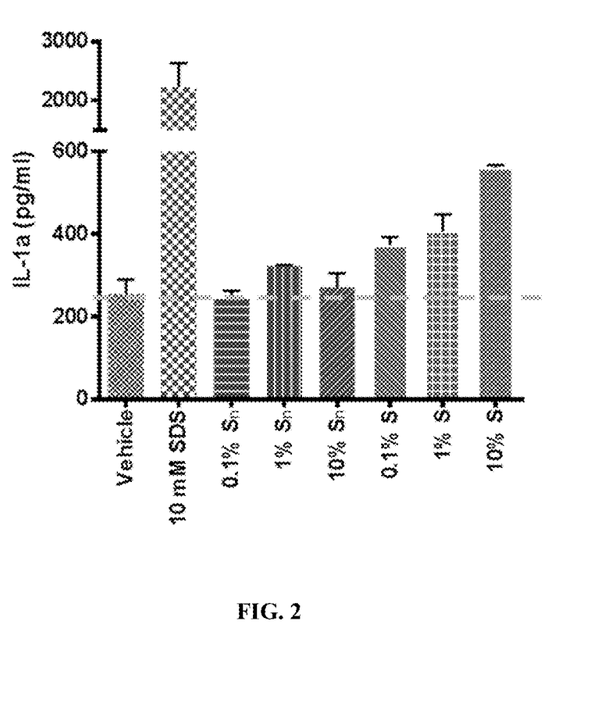
FIG. 2 is a graph depicting the results of an assay comparing the stimulation of the pro-inflammatory cytokine IL-1α in the presence of polymeric sulfur ($S_n$), at each of the doses tested of 0.1%, 1% and 10%, and in the presence of regular sulfur (S), when applied topically at 0.1%, 1% and 10%.

In FIG. 2, the regular sulfur (S), when applied topically at 0.1%, 1% and 10%, did induce the stimulation of the pro-inflammatory cytokine IL-1α in a dose-dependent manner, and to levels significantly higher than those obtained with polymeric sulfur ($S_n$), at each of the doses tested of 0.1%, 1% and 10%. In contrast, the polymeric sulfur ($S_n$) did not induce the production of IL-1α to the same extent than that of regular sulfur (S) at the same doses tested of 0.1%, 1% and 10%.

Conclusion: Polymeric sulfur ($S_n$) at 0.1-10% was milder than regular sulfur (S) in inducing pro-inflammatory cytokine IL-1α in human skin equivalents in vitro.

Example 9B. Inflammation

Comparison of effects on stimulation of pro-inflammatory cytokines IL-1α and IL-8 production by polymeric Sulfur ($S_n$) vs. regular sulfur (S) in human primary keratinocytes in-vitro.

| Polymeric sulfur | Regular sulfur | Lonza KGM-Gold BulletKit without hydrocortisone |
|---|---|---|
| 0.01% | 0% | 99.99% |
| 0.1% | 0% | 99.9% |
| 0.3% | 0% | 99.7% |
| 1% | 0% | 99% |
| 3% | 0% | 97% |

-continued

| Polymeric sulfur | Regular sulfur | Lonza KGM-Gold BulletKit without hydrocortisone |
|---|---|---|
| 0% | 0.01% | 99.99% |
| 0% | 0.1% | 99.9% |
| 0% | 0.3% | 99.7% |
| 0% | 1% | 99% |
| 0% | 3% | 97% |

The irritation/inflammatory/mildness potential of polymeric sulfur ($S_n$) and of regular sulfur (S) were evaluated in-vitro in human primary cell cultures. Normal human epidermal keratinocytes were purchased from Promocell (Heidelberg, Germany). The cells were plated in 24-well tissue culture treated plates at a density of 30,000 cells/well in Lonza KGM-Gold BulletKit without hydrocortisone (Lonza, Walkersville, Md., USA). After 48 hours, cells were treated with the actives described below: Polymeric form of sulfur (Wuxi Wanli Chemical, China) and the regular form of sulfur (Sigma-Aldrich, St Louis, Mo.) at indicated concentrations for 24 hours, following which supernatants were collected and analyzed for IL-8 and IL-1α cytokine release using MILLIPLEX®MAP kit (Millipore Corp., Billerica, Mass.).

Figure 3:
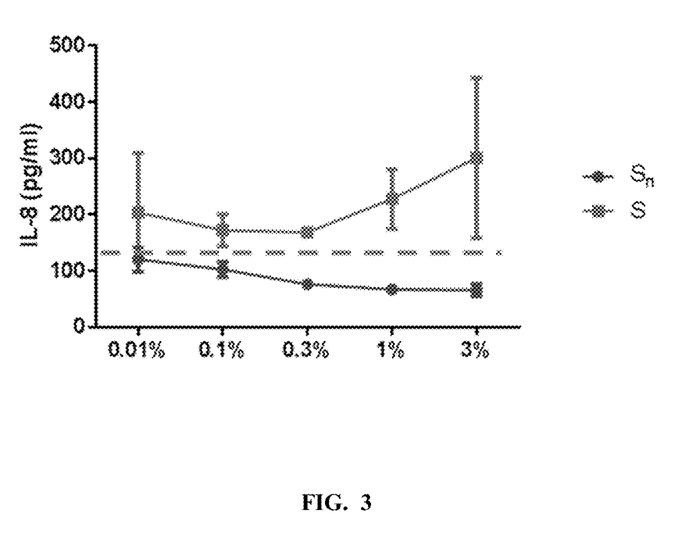
FIG. 3 is a graph depicting the results of an assay measuring the stimulation of the pro-inflammatory cytokine IL-8 above the values of the untreated control cells (dotted line) in the presence of regular sulfur (S), when used at doses ranging from 0.01% up to 3%, but not in the presence of polymeric sulfur ($S_n$).
Figure 4:
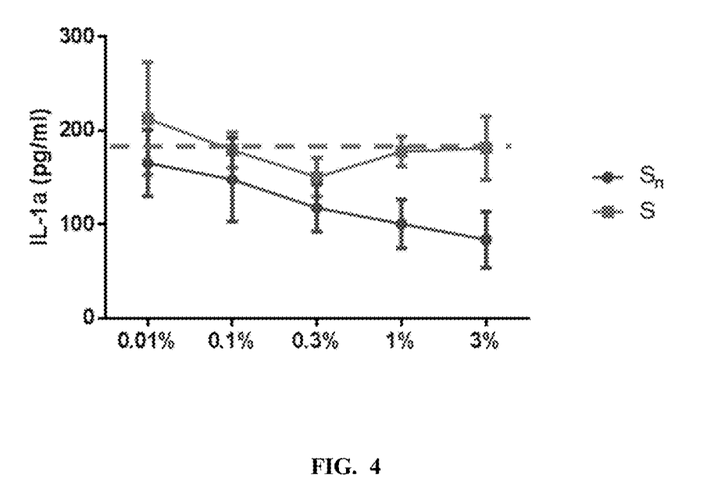
FIG. 4 is a graph depicting the results of an assay comparing the stimulation of the pro-inflammatory cytokine IL-1α in the presence of polymeric sulfur ($S_n$) and in the presence of regular sulfur (S) at the same doses tested from 0.01% up to 3%. Dotted line, untreated control cells.

In FIG. 3, regular sulfur (S), when used at doses ranging from 0.01% up to 3%, did induce significantly the stimulation of the pro-inflammatory biomarker cytokine IL-8 above the values of the untreated control cells (shown by the blue dotted line). In contrast, the polymeric sulfur ($S_n$), showed significantly lower stimulation of the pro-inflammatory cytokine IL-8 at the same doses tested from 0.01% up to 3%. In agreement with these results, the polymeric sulfur ($S_n$) showed significantly lower stimulation of the pro-inflammatory cytokine IL-1α than that of regular sulfur (S) at the same doses tested from 0.01% up to 3% (FIG. 4).

Conclusion: Polymeric sulfur ($S_n$) at 0.01-3% was milder than regular sulfur (S) in inducing pro-inflammatory biomarkers IL-8 and IL-1α in human keratinocytes in vitro.

What is claimed is:

1. A personal care composition comprising: (i) about 1% by weight polymeric sulfur $S_n$, wherein said polymeric sulfur $S_n$ is substantially free of non-cosmetic oil and n is at least 9; (ii) about 25 mM L-cysteine; and (iii) a topical carrier.

2. The personal care composition according to claim 1, wherein n is at least 100.

3. The personal care composition according to claim 1, wherein said polymeric sulfur Sn is linear in conformation.

4. The personal care composition according to claim 1, wherein said composition further comprises a resorcinol.

5. The personal care composition according to claim 1, wherein said composition further comprises an active ingredient selected from the group consisting of salicylic acid and benzoyl peroxide.

* * * * *